(12) United States Patent
Klocke et al.

(10) Patent No.: US 10,589,066 B2
(45) Date of Patent: Mar. 17, 2020

(54) COUNTING APPARATUS FOR USE IN INTERVENTIONAL PROCEDURES

(71) Applicants: Stephanie Klocke, Chandler, AZ (US); CLEARSTREAM TECHNOLOGIES LIMITED, Enniscorthy, County Wexford (IE)

(72) Inventors: Stephanie Klocke, Chandler, AZ (US); Jim C. Beasley, Phoenix, AZ (US); Justin Hall, Mesa, AZ (US); Scott Randall, Mesa, AZ (US)

(73) Assignee: CLEARSTREAM TECHNOLOGIES LIMITED, Enniscorthy, County Wexford (IE)

( * ) Notice: Subject to any disclaimer, the term of this patent is extended or adjusted under 35 U.S.C. 154(b) by 390 days.

(21) Appl. No.: 14/758,605

(22) PCT Filed: Dec. 31, 2013

(86) PCT No.: PCT/IB2013/003068
§ 371 (c)(1),
(2) Date: Jun. 30, 2015

(87) PCT Pub. No.: WO2014/102610
PCT Pub. Date: Jul. 3, 2014

(65) Prior Publication Data
US 2015/0352323 A1 Dec. 10, 2015

Related U.S. Application Data

(60) Provisional application No. 61/747,412, filed on Dec. 31, 2012.

(51) Int. Cl.
*A61M 25/01* (2006.01)
*A61B 90/00* (2016.01)
*A61M 25/00* (2006.01)

(52) U.S. Cl.
CPC ............. *A61M 25/01* (2013.01); *A61B 90/06* (2016.02); *A61M 25/0097* (2013.01); *A61M 25/0113* (2013.01); *A61M 2025/0166* (2013.01)

(58) Field of Classification Search
CPC ........ A61M 25/0113; A61M 2090/061; A61M 2090/062; A61M 90/06; B65H 61/00;
(Continued)

(56) References Cited

U.S. PATENT DOCUMENTS 1,006,473 A * 10/1911 Frank ..................... G01B 5/043
33/747
1,204,511 A * 11/1916 Smith et al. ........... G01B 5/043
33/745
(Continued)

FOREIGN PATENT DOCUMENTS

EP 0050606 A1 4/1982
EP 0850659 A1 12/1997
(Continued)

*Primary Examiner* — Kami A Bosworth
(74) *Attorney, Agent, or Firm* — King & Schickli, PLLC

(57) ABSTRACT

An apparatus is for use in connection with an implement for being inserted into a vascular space. The apparatus includes a body having a passage adapted for receiving the implement. A counter is provided for counting the amount the implement moves through the passage of the body. A kit may include a first counter adapted for use with a first device having a first diameter for being inserted into the vasculature, and a second counter adapted for use with a second device having a second diameter for being inserted into the vasculature. Related methods are also disclosed.

11 Claims, 4 Drawing Sheets

(58) Field of Classification Search
CPC ........ B65H 61/005; G01B 3/12; G01B 5/043;
G01B 5/04; G01B 5/18; G01B 7/026;
G01B 7/04; G01B 7/042; G01B 7/044;
G01B 7/046; G01B 11/04; G01B 11/043;
G01B 21/02; G01B 21/06; A61B
2090/061; A61B 2090/062
See application file for complete search history.

(56) References Cited

U.S. PATENT DOCUMENTS

| | | | |
|---|---|---|---|
| 1,223,955 A * | 4/1917 | Gant | G01B 5/043 33/745 |
| 1,225,128 A * | 5/1917 | Heimark | G01B 5/043 33/745 |
| 1,403,164 A * | 1/1922 | Hosch | G01B 5/043 33/753 |
| 3,791,038 A * | 2/1974 | Polydoris | G01B 3/12 33/780 |
| 3,835,543 A * | 9/1974 | Polydoris | G01B 3/12 33/781 |
| 4,285,131 A | 8/1981 | Demchak et al. | |
| 4,307,723 A * | 12/1981 | Finney | A61F 2/04 604/544 |
| 4,383,532 A * | 5/1983 | Dickhudt | A61N 1/0551 607/117 |
| 4,397,091 A | 8/1983 | Gustavsson et al. | |
| 4,645,491 A | 2/1987 | Evans | |
| 4,970,398 A | 11/1990 | Scheid | |
| 5,085,636 A | 2/1992 | Burns | |
| 5,092,834 A | 3/1992 | Bradshaw et al. | |
| 5,139,473 A | 8/1992 | Bradshaw et al. | |
| 5,239,982 A | 8/1993 | Trauthen | |
| 5,297,346 A | 3/1994 | Weiner | |
| 5,437,290 A | 8/1995 | Bolger et al. | |
| 5,617,858 A | 4/1997 | Taverna et al. | |
| 5,709,661 A | 1/1998 | Van Egmond et al. | |
| 5,800,333 A | 9/1998 | Liprie | |
| 6,074,367 A | 6/2000 | Hubbell | |
| 6,171,234 B1 * | 1/2001 | White | A61B 1/018 600/102 |
| 6,450,976 B2 | 9/2002 | Korotko et al. | |
| 6,497,645 B1 | 12/2002 | Halpern | |
| 7,276,044 B2 | 10/2007 | Ferry et al. | |
| 7,326,236 B2 | 2/2008 | Andreas et al. | |
| 7,603,159 B2 | 10/2009 | Rasche | |
| 7,686,816 B2 | 3/2010 | Belef et al. | |
| 2002/0198559 A1 | 12/2002 | Mistry et al. | |
| 2005/0256374 A1 | 11/2005 | Long et al. | |
| 2006/0224114 A1 | 10/2006 | van Sloten et al. | |
| 2007/0250006 A1* | 10/2007 | Court | A61B 5/064 604/117 |
| 2008/0091257 A1 | 4/2008 | Andreas et al. | |
| 2010/0198227 A1* | 8/2010 | Kim | A61B 5/1076 606/102 |
| 2011/0028941 A1* | 2/2011 | Nagano | A61B 17/12022 604/528 |

FOREIGN PATENT DOCUMENTS

| | | |
|---|---|---|
| EP | 1818071 A1 | 8/2007 |
| WO | 9945994 A1 | 9/1999 |
| WO | WO2005096797 A1 | 10/2005 |
| WO | WO2006135988 A1 | 12/2006 |
| WO | WO2007132447 A2 | 11/2007 |
| WO | 2009137410 A1 | 11/2009 |
| WO | WO2009137410 A1 | 12/2009 |

* cited by examiner

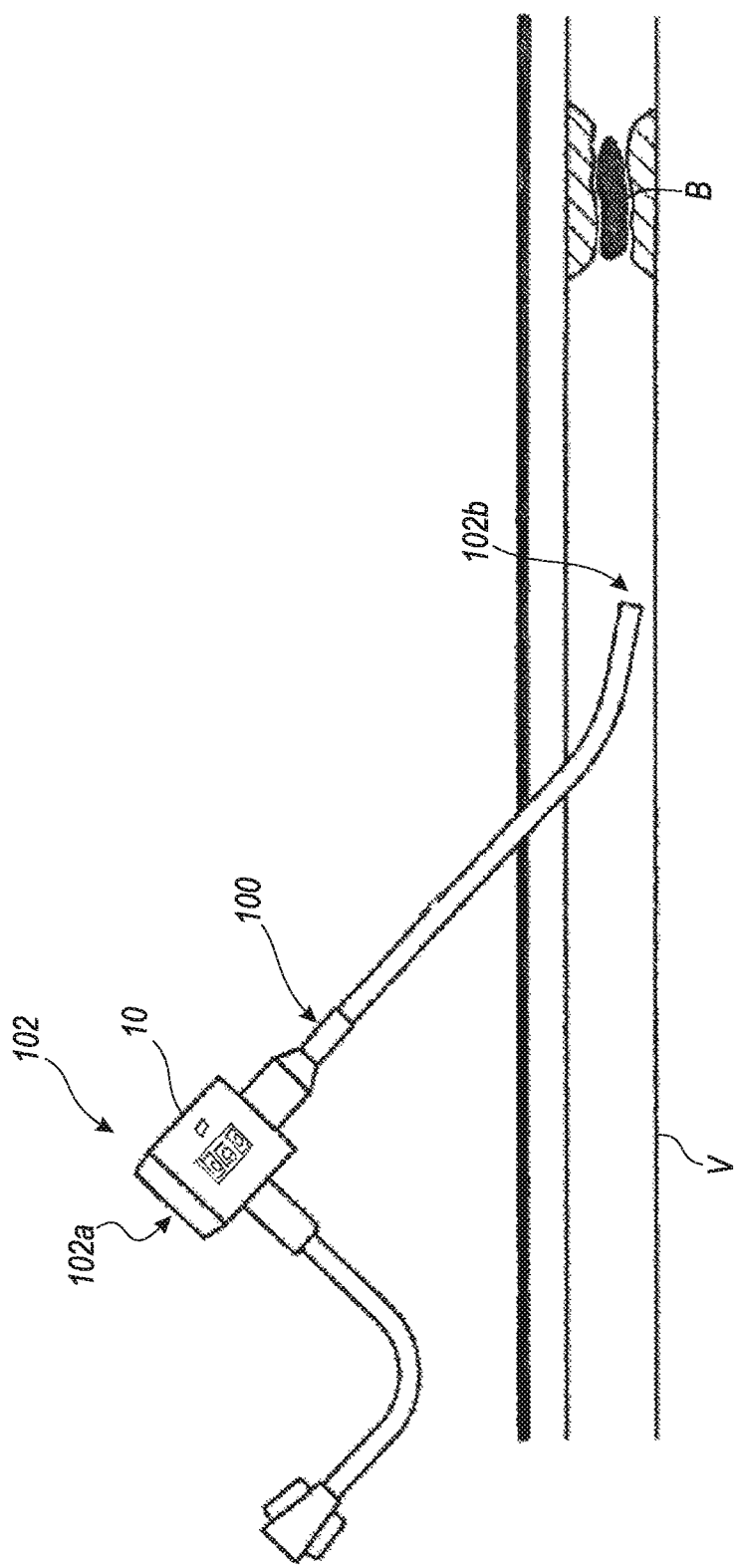

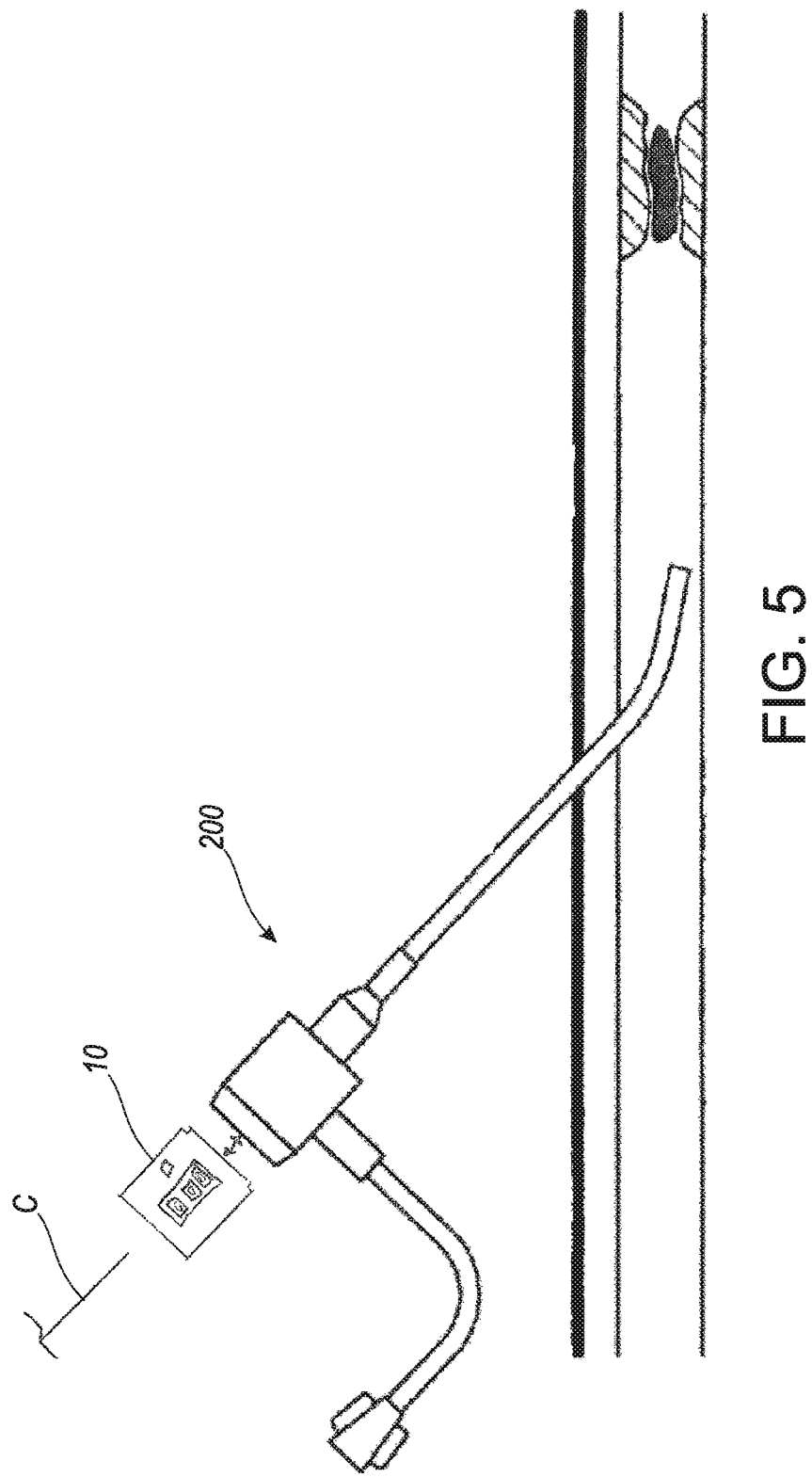

COUNTING APPARATUS FOR USE IN INTERVENTIONAL PROCEDURES

This application claims the benefit of U.S. Provisional Patent Application Ser. No. 61/747,412, which is incorporated herein by reference.

TECHNICAL FIELD

This disclosure relates generally to interventional medical procedures, such as angioplasty, and, more particularly, to a device for precisely determining the distance that a catheter, guidewire, or both, is introduced into the vasculature.

BACKGROUND OF THE INVENTION

Catheters including balloons are routinely used to resolve or address flow restrictions or perhaps even complete blockages in tubular areas of a body, such as arteries or veins. In many clinical situations, the restrictions are caused by hard solids, such as calcified plaque, and may sometimes involve the use of high pressures to compact such blockages. Commercially available balloons employ complex technology to achieve high pressure requirements without sacrificing the profile of the balloon. Besides high pressure requirements, the balloons should also be resistant to puncture, easy to track and push, and present a low profile, especially when used for angioplasty.

The clinician performing the angioplasty procedure should be able to locate the position of the uninflated balloon with accuracy, so that the balloon will be properly positioned once inflated. This is conventionally accomplished by attaching marker bands on the catheter shaft corresponding to the ends of the balloon working surface. This "working surface" is the surface along the portion of the balloon that is used to achieve the desired treatment effect, such as contacting the calcified plaque (which surface in the case of a balloon having conical or tapering sections at the proximal and distal ends is typically co-extensive with a generally cylindrical barrel section).

However, misalignment of the marker bands during placement along the shaft sometimes results in their failure to correspond precisely to the extent of the working surface. This misalignment may prevent the clinician from accurately identifying the location of the working surface of the balloon during an interventional procedure. Also, when successive intravascular interventions are made, such as during a pre-dilatation using a first catheter followed by dilatation using a second catheter, the clinician must guess where the pre-dilatation occurred. In either case, this uncertainty may lead to a geographic misalignment, or "miss," of the intended contact between the intended treatment area and the working surface of the balloon. It is especially desirable to avoid such an outcome when the balloon is designed to deliver a payload (such as a therapeutic agent (e.g. a drug, such as paclitaxel, rapamycin, heparin and the like), a stent, a stent graft, or a combination thereof) or a working element (such as a cutter, focused force wire, or the like) to a specified location within the vasculature, since a miss may, at a minimum, prolong the procedure (such as, for example, by requiring redeployment of the balloon or the use of another balloon catheter in the case of a drug coated balloon), and result in an inferior outcome if the lesion is not properly treated due to the misalignment.

Accordingly, there is a need for a manner in which to introduce a catheter or other implement into the vasculature with enhanced precision, and in a manner that is highly repeatable, yet without considerable expense or complication.

SUMMARY OF THE INVENTION

An object of the disclosure is to provide a counter for counting the distance that an implement for use in performing a PTA procedure may be introduced during an interventional procedure. This distance measurement may then be used to ensure the accuracy of placement of other implements (e.g. a drug, a drug-coated balloon, a stent, a drug-eluting stent, a cutter, a focused-force wire, or any combination of the foregoing).

In one aspect, the disclosure pertains to an apparatus for use in connection with an implement for being inserted into a vascular space. The apparatus comprises a body having a passage adapted for receiving the implement, and a counter for counting the amount the implement moves through the passage of the body.

The counter may comprise a tracking device connected to the body and interfacing with the implement to track the movement of the implement through the passage. The tracking device may comprise one or more rollers projecting into the passage and arranged for engaging the body, and/or may comprise a sensor. The counter may comprise comprises at least one wheel including a plurality of numbers, said wheel being rotated in response to the tracking device tracking the movement of the implement.

The counter may be provided on the body, and may be adapted for use with a catheter as the implement. Alternatively, the counter may be adapted for use with a guidewire as the implement. The body may be adapted for being releasably connected to an introducer for introducing the implement to the vascular area. In any of the embodiments, the body may be tubular, and may include an introducer.

A further aspect of the disclosure thusly pertains to an introducer for introducing an implement into a vascular space, said introducer comprising a counter for counting the movement of the implement. The introducer may include a first end carrying the counter. The first end may comprise a tubular body having a passage adapted for receiving the implement. The tubular body may be removably attached, or may be permanently attached.

The disclosure thusly also pertains to a kit comprised of a first catheter adapted for performing a first intervention at a first location in the vasculature, and a second catheter adapted for performing a second intervention at the first location. A counter adapted for sequentially counting an introduction amount of the first catheter and the second catheter is also provided.

A further aspect of the disclosure relates to a kit including a first counter adapted for use with a first device having a first diameter for being inserted into the vasculature, and a second counter adapted for use with a second device having a second diameter for being inserted into the vasculature Still another aspect of the disclosure relates to a a method of performing a procedure in the vasculature. The method comprises performing a first intervention at a first location in the vasculature and, during the first intervention, using a counter to determine an amount of the first catheter introduced to reach the first location. During a second intervention, the step of using the determined amount to reach the first location accurately is performed.

In one embodiment, performing the first intervention comprises inserting a first catheter, and performing the second intervention comprises inserting a second catheter.

The method may further include the step of resetting the counter to zero after the insertion of the first catheter, but before it is withdrawn, and then causing the counter to count down during the withdrawal of the first catheter, and then counting up when the second catheter is inserted to the first location. Still further, the method may include inserting the second catheter including a treatment selected from the group consisting of a balloon, a drug, a drug-coated balloon, a stent, a drug-eluting stent, a cutter, a focused-force wire, or any combination of the foregoing.

Yet another aspect of the disclosure relates to an apparatus for use in connection with an implement for being inserted into a vascular space. The apparatus comprises a body having a passage adapted for receiving the implement and including at least three radially projecting rollers arranged circumferentially for engaging the implement.

A further aspect of the disclosure relates to an apparatus for use in connection with an implement for being inserted into a vascular space. The apparatus comprises a body having a passage adapted for receiving the implement, and a counter connected to the body for counting and displaying the amount the implement moves through the passage of the body.

Still a further aspect of the disclosure relates to an apparatus for use in connection with an implement for being inserted into a vascular space. The apparatus comprises a portable, disposable body having a passage adapted for receiving the implement; and a mechanical counter for counting and displaying the amount the implement moves through the passage of the body.

Furthermore, the disclosure relates to an apparatus for use in connection with an implement for being inserted into a vascular space. The apparatus comprises a body having a passage adapted for receiving the implement and adapted for being connected to an introducer for introducing the implement to the vascular space, and a counter for counting the amount the implement moves through the passage of the body.

BRIEF DESCRIPTION OF THE FIGURES

FIGS. 3 and 4 show a way of using a device according to an embodiment of the present disclosure.

FIG. 5 shows a further way of using a device according to an embodiment of the present disclosure.

MODES FOR CARRYING OUT THE INVENTION

The description provided below and in regard to the figures applies to all embodiments unless noted otherwise, and features common to each embodiment are similarly shown and numbered.

Figure 2:
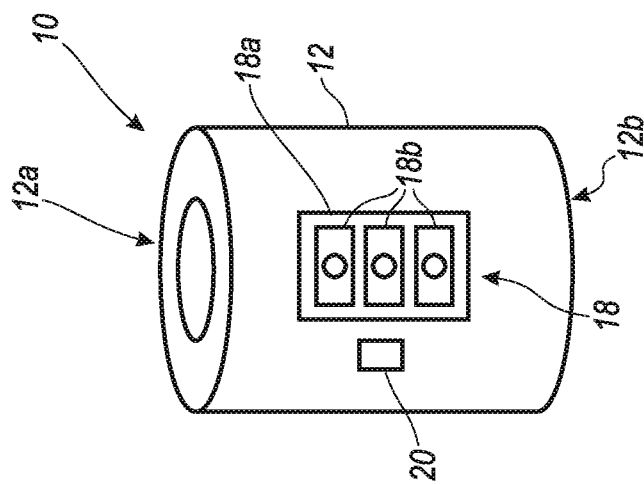
FIGS. 1 and 2 show a device according to an embodiment of the present disclosure.
Figure 1:
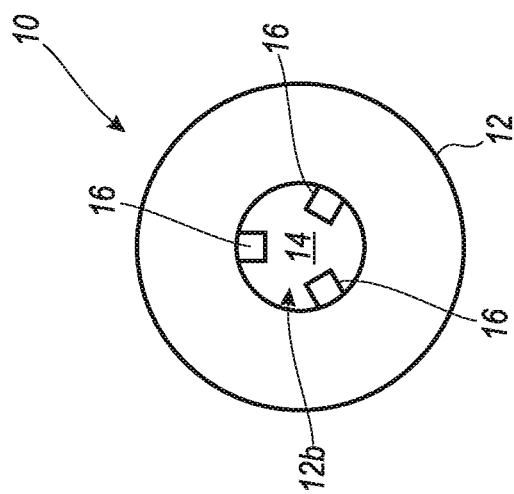

With reference to FIGS. 1 and 2, a device 10 is provided for measuring the distance that an implement, such as a catheter (see FIG. 4) is introduced into the vasculature during an interventional procedure. In the illustrated embodiment, the device 10 comprises a body 12, which may be generally cylindrical in shape but could take other forms (e.g., cubic). The body 12 includes a passage 14 including an inlet 12a adapted for receiving the implement and an outlet 12b through which it may pass. The diameter and shape of the passage 14 may be chosen to correspond to the particular implement being used with it, such as a balloon catheter, a guide wire, or the like.

The body 12 further includes one or more tracking devices for tracking the relative movement of the implement through the passage. In one embodiment, as shown, the tracking devices comprise a plurality of rollers 16 oriented in the circumferential direction at intervals of approximately 120 degrees, and projecting into the passage 14 a distance such that low friction, rolling contact is established with the external surface of the implement as it passes. The contact may be enhanced by including a spring or like device to urge one or more of the rollers 16 toward the center of the passage 14, but the force should be tempered so that the progress of the implement is not retarded as a result.

In any case, the resulting engagement causes the rollers 16 to rotate due to the rolling friction. By counting the number of revolutions, the amount (which may or may not correspond to a linear distance) that the implement passes through the passage 14 may be determined. This amount may then be displayed to the user, such as by providing a display 18 on the body 12 (but the display could also be on a separate structure). The amount may be in particular units (e.g., millimeters, centimeters, inches, or any portions thereof), or instead may simply be an arbitrary unit (in cases where the distance is used to determine the amount of introduction of two substantially identical devices). Also, the amount could be displayed in positive units, negative units, or both, and may count in either direction.

The counting may be done electronically, such as using a proximity sensor to determine the rotations of the rollers 16, or may be done mechanically using gears. In the case of gears, the arrangement may be such that a gear connected to at least one of the rollers 16 rotates one or more numerical wheels 18 $b$ forming part of a counter 18 $a$ to display a count, such as in Arabic numerals. In the illustrated embodiment, three such wheels 18 $b$ are shown, which thus allow for a three digit number to be displayed (with gearing such that each full rotation of one wheel causing the next one to advance, similar to an odometer; see, e.g., U.S. Pat. No. 4,970,378), but any number could be used. Alternatively, the counter 18 $a$ may comprise an electronic display, such as an LED, LCD, or the like, which could be provided remote from the body 12 (with wireless transmission of the resulting amounts for display). A reset 20, such as a button, may also be provided to erase the count, such as by returning the wheels 18 $b$ to the home (e.g., zero) position, or erasing any electronic display.

Figure 4:
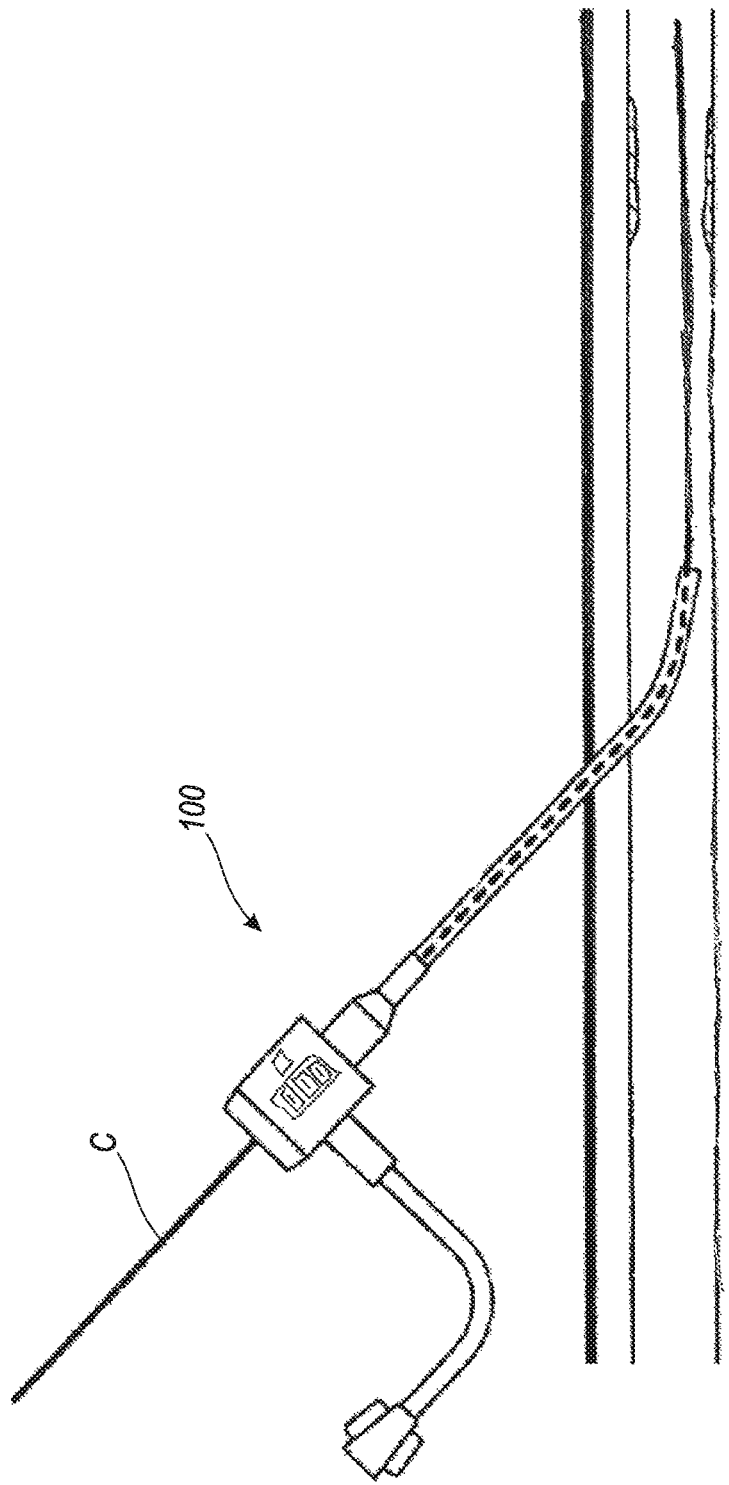

Turning to FIGS. 3-5, different manners of using the device are shown. In the arrangement of FIGS. 3 and 4, the device 10 forms part of an introducer 100 for introducing a catheter into the vasculature, such as a vessel V, in a percutaneous manner. The introducer 100 includes a first end 102 including the device 10 and a mouth or inlet 102a for receiving an implement for being introduced into the vessel V, such as a catheter C. An outlet 102b at the other end of the introducer 100 passes, or "introduces," the implement, such as catheter C, to the vessel, and further facilitates withdrawal. As should be appreciated, the advancement and retraction of the catheter C may cause the counter 18 to display a reading according to the linear distance it travels through the passage 14 associated with the device 10.

In a second embodiment, as shown in FIG. 5, the device 10 is a modular structure that may be attached to the proximal end of an introducer 200. The body 12 and the introducer 200 may be adapted for forming a connection, such as by providing male/female connectors (e.g., a socket/plug arrangement, bayonette fitting, snap-fit, press fit, friction fit, harness (including a band or the like for wrapping around the mouth of the introducer), or like secure, but temporary connection). Advantageously, this allows for the device 10 to be used with a plurality of different introducers adapted to interface with the body 12.

One method of using the device 10 is to insert a first catheter into a vessel to a predetermined location or treatment area, such as a blockage B. The first catheter may be at least partly radiopaque, and thus may allow the clinician to assess the location of the treatment area within the vasculature relative to the first catheter through device (with or without introducer 100, 200) when introduced under fluoroscopy. The first catheter may then be withdrawn and, based on the distance determined using the device 10, a second catheter, such as one carrying a treatment (such as a therapeutic agent (e.g., a drug), a drug-coated balloon, a stent, a stent graft, a drug-eluting stent, a cutter, a focused-force wire, or any combination of the foregoing) may be inserted through the device 10 to the same location, as determined by matching the count on display 18. In any event, this helps to ensure that the same exact location is reached during each intervention, and helps to avoid the problem of geographic misalignment. A corresponding kit may also be provided.

As an alternative, the display 18 could be reset after the first intervention, but before the implement, such as catheter C, is withdrawn from the device 10. Withdrawal of the implement would then cause the display 18 to count a negative amount. Introduction of a second implement, such as a second catheter, would then cause the count to increase from the negative number to zero when the correct location is reached.

It should also be appreciated that multiple devices 10 may be adapted for different implements. For instance, a first device may be adapted for determining the distance a first implement, such as a guidewire is introduced. This first device may have a narrower passage and correspondingly arranged tracking devices, since a guidewire is typically of a relatively small diameter. A second device adapted for a second implement, such as a catheter, may then be substituted (such as by sleeving the first device along the proximal end of the guidewire and replacing it with the second device) with the same introducer and calibrated such as to create a corresponding distance measurement. Hence, if a guidewire with one or more radiopaque markers is introduced, and a catheter with a radiopaque marker is introduced in an attempt to align and register the two at a particular location, the second device may be used to confirm the relative distances traveled.

The device 10 may be a relatively small, portable device, such as for example having a length of 1-2 cm and a diameter of 1-2 cm. The device 10 may be made of plastic parts and, thus, may be made for use in a single medical procedure and then discarded. Alternatively, the device may be made for re-use.

While the disclosure presents certain embodiments to illustrate the inventive concepts, numerous modifications, alterations, and changes to the described embodiments are possible without departing from the sphere and scope of the present invention, as defined in the appended claims. For example, any ranges and numerical values provided in the various embodiments are subject to variation due to tolerances, due to variations in environmental factors and material quality, and due to modifications of the structure and shape of the balloon, and thus can be considered to be approximate and the term "approximately" means that the relevant value can, at minimum, vary because of such factors. Also, the drawings, while illustrating the inventive concepts, are not to scale, and should not be limited to any particular sizes or dimensions. Accordingly, it is intended that the present disclosure not be limited to the described embodiments, but that it has the full scope defined by the language of the following claims, and equivalents thereof.

The invention claimed is:

1. An apparatus for use in connection with an implement for being inserted into a vascular space, comprising:
   a single use device comprising a plastic tubular body having a first end wall, a second end wall and a sidewall defining an interior passage extending from the first end wall to the second end wall and adapted for receiving the implement;
   a counter for engaging the implement within the interior passage for counting an amount the implement moves through the interior passage of the tubular body; and
   a display for displaying the amount on the sidewall of the tubular body, the display comprising a plurality of wheels, each of the plurality of wheels having numbers for indicating the amount the implement moves through the interior passage of the tubular body.

2. The apparatus of claim 1, wherein the counter comprises a tracking device connected to the tubular body and adapted for interfacing with the implement to track the amount the implement moves through the interior passage.

3. The apparatus of claim 2, wherein the tracking device comprises one or more rotatable rollers projecting into the interior passage and arranged for engaging the implement.

4. The apparatus of claim 1, wherein the counter is adapted for use with a catheter as the implement.

5. The apparatus of claim 1, wherein the counter is adapted for use with a guidewire as the implement.

6. The apparatus of claim 1 wherein the counter comprises three radially projecting rollers arranged circumferentially around the interior passage at intervals of approximately 120 degrees for engaging the implement when positioned in the interior passage.

7. The apparatus of claim 1 wherein the tubular body is annular.

8. The apparatus of claim 1, wherein the interior passage includes an inlet at the first end wall and an outlet at the second end wall of the tubular body.

9. The apparatus of claim 1, wherein the device has a length of 1-2 cm and a diameter of 1-2 cm.

10. A kit, comprising:
    the apparatus of claim 1;
    a first catheter adapted for performing a first intervention at a first location in the vascular space; and
    a second catheter adapted for performing a second intervention at the first location.

11. An apparatus for use in connection with an implement for being inserted into a vascular space, comprising:
    an introducer for introducing the implement to the vascular space;
    a single use device comprising a tubular body having an interior passage adapted for receiving the implement, the tubular body having a first end wall, a second end wall and a sidewall defining the interior passage extending from the first end wall to the second end wall and adapted for being connected to the introducer for introducing the implement to the vascular space;
    a counter for counting an amount the implement moves through the interior passage of the tubular body; and
    a display for displaying the amount on the sidewall of the tubular body.

* * * * *